(12) United States Patent
Strehl et al.

(10) Patent No.: US 9,592,348 B2
(45) Date of Patent: Mar. 14, 2017

(54) ASSEMBLY FOR A DRUG DELIVERY DEVICE AND DRUG DELIVERY DEVICE

(71) Applicant: Sanofi-Aventis Deutschland GmbH, Frankfurt am Main (DE)

(72) Inventors: Michael Strehl, Pfremid (DE); Udo Leuschner, Regensburg (DE); Norbert Besenhardt, Teublitz (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 15/139,025

(22) Filed: Apr. 26, 2016

(65) Prior Publication Data
US 2016/0235921 A1    Aug. 18, 2016

Related U.S. Application Data

(63) Continuation of application No. 14/887,736, filed on Oct. 20, 2015, now Pat. No. 9,486,587, which is a (Continued)

(30) Foreign Application Priority Data
Jun. 2, 2009  (EP) .................................... 09007297

(51) Int. Cl.
A61M 5/315 (2006.01)
A61M 5/24 (2006.01)
A61M 5/31 (2006.01)

(52) U.S. Cl.
CPC ...... A61M 5/31536 (2013.01); A61M 5/3155 (2013.01); A61M 5/31511 (2013.01);
(Continued)

(58) Field of Classification Search
CPC .......... A61M 5/31511; A61M 5/31536; A61M 5/31541; A61M 5/31551; A61M 5/31555;
(Continued)

(56) References Cited
U.S. PATENT DOCUMENTS 533,575 A    2/1895  Wilkens
5,226,895 A   7/1993  Harris
(Continued)

FOREIGN PATENT DOCUMENTS

CN    101227942    7/2008
DE    20023819     7/2006
(Continued)

OTHER PUBLICATIONS

Bibliographic data of the European Patent Application No. 10723101.1 dated Jan. 7, 2013.
(Continued)

*Primary Examiner* — Laura Bouchelle
*Assistant Examiner* — Justin L Zamory
(74) *Attorney, Agent, or Firm* — McDonnell Boehnen Hulbert & Berghoff LLP

(57) ABSTRACT

An assembly for a drug delivery device, and a drug delivery device, are proposed with a housing having proximal and distal ends. A dose member is displaceable proximally with respect to the housing for setting of a dose of a drug. A clutch member is displaceable proximally with respect to the housing when setting the dose. A stop member is configured to define a clutch stop position for the proximal displacement of the clutch member with respect to the housing, the clutch member, when in the clutch stop position, is prevented from further displacement proximally with respect to the housing, and the clutch member and the dose member are configured to mechanically cooperate with one another when the clutch member is in the clutch stop position, thereby preventing further displacement of the dose member proximally with respect to the housing during setting of the dose.

30 Claims, 8 Drawing Sheets

Related U.S. Application Data continuation of application No. 13/375,441, filed as application No. PCT/EP2010/057633 on Jun. 1, 2010.

(60) Provisional application No. 61/239,557, filed on Sep. 3, 2009.

(52) U.S. Cl.
CPC .... *A61M 5/31541* (2013.01); *A61M 5/31551* (2013.01); *A61M 5/24* (2013.01); *A61M 5/3158* (2013.01); *A61M 5/31556* (2013.01); *A61M 5/31561* (2013.01); *A61M 5/31586* (2013.01); *A61M 2005/2407* (2013.01); *A61M 2005/2488* (2013.01); *A61M 2005/3104* (2013.01)

(58) Field of Classification Search
CPC .......... A61M 5/31556; A61M 5/31561; A61M 5/31586; A61M 2005/3104; A61M 2005/2403; A61M 2005/2407; A61M 2005/3154
See application file for complete search history.

(56) References Cited

U.S. PATENT DOCUMENTS

| | | |
|---|---|---|
| 5,279,586 A | 1/1994 | Balkwill |
| 5,304,152 A | 4/1994 | Sams |
| 5,320,609 A | 6/1994 | Haber |
| 5,383,865 A | 1/1995 | Michel |
| 5,480,387 A | 1/1996 | Gabriel |
| 5,505,704 A | 4/1996 | Pawelka |
| 5,582,598 A | 12/1996 | Chanoch |
| 5,626,566 A | 5/1997 | Petersen |
| 5,674,204 A | 10/1997 | Chanoch |
| 5,688,251 A | 11/1997 | Chanoch |
| 5,921,966 A | 7/1999 | Bendek |
| 5,961,495 A | 10/1999 | Walters |
| 6,004,297 A | 12/1999 | Steenfeldt-Jensen et al. |
| 6,193,698 B1 | 2/2001 | Kirchhofer |
| 6,221,046 B1 | 4/2001 | Burroughs |
| 6,235,004 B1 | 5/2001 | Steenfeldt-Jensen et al. |
| 6,248,095 B1 | 6/2001 | Giambattista |
| 6,582,404 B1 | 6/2003 | Klitgaard |
| 6,899,698 B2 | 5/2005 | Sams |
| 6,936,032 B1 | 8/2005 | Bush |
| 7,169,132 B2 | 1/2007 | Bendek et al. |
| 7,241,278 B2 | 7/2007 | Møller |
| 8,491,538 B2 | 7/2013 | Kohlbrenner et al. |
| 8,920,383 B2 | 12/2014 | Enggaard et al. |
| 9,089,652 B2 | 7/2015 | Nzike et al. |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0127858 A1 | 7/2004 | Bendek et al. |
| 2004/0210199 A1 | 10/2004 | Atterbury et al. |
| 2004/0260247 A1 | 12/2004 | Veasey et al. |
| 2004/0267207 A1 | 12/2004 | Veasey et al. |
| 2005/0033244 A1 | 2/2005 | Veasey et al. |
| 2005/0113765 A1 | 5/2005 | Veasey |
| 2006/0153693 A1 | 7/2006 | Fiechter |
| 2007/0016142 A1 | 1/2007 | Burren |
| 2008/0234634 A1 | 9/2008 | Eiland et al. |
| 2009/0054851 A1 | 2/2009 | Radmer et al. |
| 2009/0275916 A1* | 11/2009 | Harms .................... A61M 5/24 604/506 |
| 2010/0152672 A1 | 6/2010 | Raab |
| 2014/0194830 A1 | 7/2014 | Nzike et al. |

FOREIGN PATENT DOCUMENTS

| | | |
|---|---|---|
| DE | 102005023823 | 11/2006 |
| EP | 0937476 | 2/1998 |
| EP | 0937471 | 2/1999 |
| EP | 1304129 | 4/2003 |
| GB | 0304823.8 | 3/2003 |
| GB | 03024822 | 3/2003 |
| JP | 2006501026 | 1/2006 |
| JP | 2008529690 | 8/2008 |
| JP | 2009502273 | 1/2009 |
| JP | 2009502274 | 1/2009 |
| JP | 2010503433 | 2/2010 |
| JP | 2012511358 | 5/2012 |
| KR | 10-2007-0048750 | 9/2007 |
| TW | 200507897 | 3/2005 |
| WO | 9938554 | 8/1999 |
| WO | 0110484 | 2/2001 |
| WO | 0172361 | 10/2001 |
| WO | 02092153 | 11/2002 |
| WO | 2004078239 | 9/2004 |
| WO | 2006024461 | 3/2006 |
| WO | 2007017052 | 2/2007 |
| WO | 2007017053 | 2/2007 |
| WO | 2008031235 | 3/2008 |
| WO | 2008031238 | 3/2008 |
| WO | 2010139691 | 12/2010 |

OTHER PUBLICATIONS

Communication about Intention to grant a European patent sent to Sanofi-Aventis Deutschland GmbH dated Jan. 7, 2013.
Intention to Grant (Signatures) dated Jan. 7, 2013.
Text intended for Grant dated Jan. 7, 2013.
Notification on Forthcoming Publication of Bibliographic Data sent to Sanofi-Aventis Deutschland GmbH dated Mar. 14, 2012.
Communication regarding Comments on Written Opinion/Amendment of Application/Payment of claims fee sent to Sanofi-Aventis Deutschland GmbH dated Jan. 17, 2012.
The International Preliminary Report on Patentability dated Dec. 27, 2011.
Acknowledgement of Receipt for European Patent Application No. 10723101.1 dated Dec. 6, 2011.
Request for Entry into the European Phase dated Dec. 6, 2011.
Information on Entry int o the European Phase sent to Sanofi-Aventis Deutschland GmbH dated Oct. 14, 2011.
Certified priority document of European Patent Application No. 09007297.6 dated Dec. 31, 2010.
Certified priority document of U.S. Appl. No. 61/239,557 dated Dec. 31, 2010.
International Search Report issued in International Patent Application No. PCT/EP2010/057633 dated Dec. 9, 2010.
Notification Concerning Transmittal of International Preliminary Report on Patentability, dated Dec. 15, 2011 (5 pages).
Extended European Search Report issued in European Patent Application No. 09007297.6 dated Dec. 11, 2009.
Form PCT/ISA/220, Notification of Transmittal of the International Search Report and the Written Opinion of the International Searching Authority, or the Declaration dated Aug. 18, 2010.
English Translation of Notification of Reasons for Refusal issued in Japanese Patent Application No. 2012-513599 dated Mar. 31, 2014.
Patent Examination Report No. 1 issued in Australian Patent Application No. 2010255777 dated Apr. 11, 2014.
Advise of Delivery in European Patent Application No. 10723101.1 sent to Samson & Partner dated Oct. 16, 2015.
Advise of Delivery sent to Samson & Partner dated Sep. 29, 2015.
Advise of Delivery sent to Keil & Schaafhausen dated Sep. 26, 2015.
Advise of Delivery in European Patent Application No. 10723101.1 sent to Keil & Schaafhausen dated Sep. 26, 2015.
Annex to the Communication-Opposition-issued in European Patent No. 10723101.1 dated Sep. 22, 2015.
Information concerning oral proceeding issued in European Patent Application No. 10723101.1 sent to Samson & Partner dated Sep. 22, 2015.
Information concerning oral proceeding issued in European patent Application No. 10723101.1 sent to Keil & Schaafhausen dated Sep. 22, 2015.

(56) References Cited

OTHER PUBLICATIONS

Preparation for Oral Proceedings issued in European Patent Application No. 10723101.1 dated Sep. 22, 2015.
Summons to attend oral proceedings issued in European Patent Application No. 10723101.1 sent to Keil & Schaafhausen dated Sep. 22, 2015.
Summons to attend oral proceedings issued in European Patent Application No. 10723101.1 sent to Samson & Partner dated Sep. 22, 2015.
Brief communication regarding opposition proceedings issued in European Patent Application No. 10723101.1 sent to Keil & Schaafhausen dated Aug. 24, 2015.
Brief communication regarding opposition proceedings issued in European Patent Application No. 10723101.1 sent to Samson & Partner dated Aug. 20, 2015.
Keil & Schaafhausen Request for Interpreters during oral proceedings dated Aug. 20, 2015.
Samson & Partner Request for Interpreters during oral proceedings dated Aug. 20, 2015.
Brief communication-opposition proceedings sent to Samson & Partner dated Aug. 12, 2015.
Brief Communication of Opposition proceedings issued in European Patent Application No. 10723101.1 sent to Keil & Schaafhausen dated Aug. 12, 2015.
Brief Communication of Opposition proceedings issued in European Patent Application No. 10723101.1 sent to Keil & Schaafhausen dated Apr. 17, 2015.
Communication of Amended Entries issued in European Patent Application No. 10723101.1 sent to Samson & Partner dated Apr. 17, 2015.
Request for Change of Opponents Representative sent by Samson & Partner dated Apr. 2, 2015.
Amended Claims with Annotations dated Dec. 10, 2014.
Brief Communication-Opposition Proceeding issued in European Patent Application No. 10723101.1 sent to Samson & Partner dated Oct. 10, 2014.
Claims dated Dec. 10, 2014.
Reply of the Patent Proprietor to the Notice(s) of Opposition sent by Keil & Schaafhausen dated Dec. 10, 2014.
Amended Claims with Annotations dated Dec. 9, 2014.
Claims dated Dec. 9, 2014.
Reply of the Patent Proprietor to the Notice(s) of Opposition sent by Keil & Schaafhausen dated Dec. 9, 2014.
Brief Communication Opposition Proceeding issued in European Patent Application No. 10723101.1 dated Oct. 10, 2014.
Grant of Extension of Time Limit issued in European Patent Application No. 10723101.1 dated Oct. 10, 2014.
Request for Extension of Time Limit sent by Keil & Schaafhausen dated Oct. 6, 2014.
Brief Communication Opposition Proceedings issued in European Patent Application No. 10723101.1 sent to Samson & Partner dated Jun. 24, 2014.
Communication of Amended Entries Concerning the Representative sent to Keil & Schaafhausen dated Jun. 24, 2014.
General Authorization sent to Keil & Schaafhausen dated Jun. 18, 2014.
Request for Change of Applicant's Representative sent by Keil & Schaafhausen dated Jun. 18, 2014.
Communication of Notice of Opposition and Request to file Observations sent to Sanofi-Aventis Deutschland GmbH dated Jun. 30, 2014.
Notice of further opposition to opponent(s) sent to Samson & Partner dated Jun. 3, 2014.
Communication of a Notice of Opposition and First Information to Patent Proprietor sent to Sanofi-Aventis Deutschland GmbH dated May 7, 2014.
Letter regarding the Opposition Procedure (no time limit) sent by Samson & Partner dated Apr. 24, 2014.
Notice of Opposition dated Apr. 24, 2014.
Payment of Fees and Expenses from Samson & Partner dated Apr. 24, 2014.
Client Database System (CDS)—Clean up, amended applicant details dated Feb. 3, 2014.
Transmission of the Certificate for a European Patent sent to Sanofi-Aventis Deutschland GmbH dated Jul. 26, 2013.
Decision to Grant a European patent sent to Sanofi-Aventis Deutschland GmbH dated Jun. 27, 2013.
Communication regarding the forthcoming Grant sent to Sanofi-Aventis Deutschland GmbH dated May 14, 2013.
Filing of the Translations of the Claims sent by Sanofi-Aventis Deutschland GmbH dated Mar. 5, 2013.
French translation of the claims dated May 3, 2013.
German translation of the claims dated May 3, 2015.

* cited by examiner

ASSEMBLY FOR A DRUG DELIVERY DEVICE AND DRUG DELIVERY DEVICE

CROSS REFERENCE TO RELATED APPLICATIONS

The present application is a continuation application of U.S. patent application Ser. No. 14/887,736, filed Oct. 20, 2015 which is also a continuation application of U.S. patent application Ser. No. 13/375,441, filed Oct. 25, 2011, which is a 371 of International Patent Application No. PCT/EP2010/057633, filed Jun. 1, 2010 which claims the benefit of European Patent Application No 09007297.6, filed Jun. 2, 2009 and U.S. Provisional Patent Application No. 61/239,557, filed Sep. 3, 2009 the entire contents of which are incorporated entirely herein by reference.

The present disclosure relates to an assembly for a drug delivery device and a drug delivery device.

Drug delivery devices may be used for self-administration of a drug contained in the device by a patient. For this purpose, the user may set a dose of drug to be delivered and deliver the dose subsequently. As the amount of drug present in the device may be limited, it may occur that the user sets a desired dose which exceeds the actually available amount of drug in the device. Accordingly, if the user administers this set dose, the user might be of the wrong opinion that the desired amount was administered.

It is an object of the present disclosure to provide for an assembly that facilitates provision of an improved drug delivery device and a drug delivery device comprising such an assembly.

This object is achieved by an assembly according to the independent claim. Advantageous embodiments and refinements may be the subject matter of dependent claims.

According to one aspect, an assembly for a drug delivery device comprises a housing having a proximal end and a distal end, a dose member which is displaceable in the proximal direction with respect to the housing for setting of a dose of a drug, a clutch member which is displaced in the proximal direction with respect to the housing when setting the dose and a stop member configured to define a clutch stop position for the proximal displacement of the clutch member with respect to the housing, with the clutch member, when in the clutch stop position, being prevented from further displacement in the proximal direction with respect to the housing. Preferably, the clutch member and the dose member are configured to mechanically cooperate with one another when the clutch member is in the clutch stop position, thereby, in particular during mechanical cooperation, preventing further displacement of the dose member in the proximal direction with respect to the housing, in particular during setting of the dose.

A drug delivery device expediently comprises an assembly as described above. The drug delivery device may comprise a cartridge containing a drug. The cartridge may have a proximal end and a distal end. A piston may be retained within the cartridge. The piston may close the cartridge proximally. The piston is preferably displaceable in the distal direction with respect to the cartridge for dispensing a dose of the drug from the cartridge. The assembly is preferably an end stop assembly. The end stop assembly may prevent setting of a desired dose of the drug, which desired dose would exceed the amount of drug which is currently available in the cartridge for delivery. The position of the stop member with respect to the distal end of the cartridge may be indicative of the amount of drug currently available in the cartridge. As one or more doses of the drug are dispensed from the cartridge, the stop member may successively be displaced towards the distal end of the cartridge, thereby indicating that less drug is left in the cartridge.

As the drug delivery device preferably comprises an assembly as described above, features which are described in connection with the drug delivery device may also apply for the assembly and vice versa.

Accordingly, by means of the assembly, setting of a dose of the drug which exceeds the actually available amount of drug may be prevented on account of the clutch member mechanically cooperating with the dose member, for example by engagement. Thereby, the risk of administering an amount of drug which is less than the set dose is reduced. During mechanical cooperation, an engagement member of the clutch member may engage an engagement feature of the dose member.

The term "drug", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp- Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;

or an Exendin-4 derivative of the sequence

H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

In a preferred embodiment, the assembly comprises a clutch spring member. The clutch spring member may be configured for and, in particular, arranged to prevent the dose member from cooperating mechanically with the clutch member. The clutch spring member may prevent the dose member from cooperating mechanically with the clutch member when the clutch member is out of the clutch stop position. The clutch spring member may bias the dose member and the clutch member away from one another. In particular, the clutch spring member may keep engagement feature and engagement member at a predetermined distance with respect to each other when the clutch member is out of the clutch stop position.

In another preferred embodiment, the dose member is rotated in a first direction with respect to the housing for setting of the dose of the drug and, in particular, displaced in the proximal direction when rotating in the first direction. The dose member may be threadedly connected to the housing, such as threadedly engaged with the housing or an insert thereof, for this purpose. Rotation of the dose member in the first direction with respect to the housing may be prevented or stopped when the dose member and the clutch member cooperate mechanically.

The dose member may be displaced in the distal direction with respect to the housing when delivering the dose and, in particular, rotate in a second direction, opposite to the first direction when delivering the dose.

In another preferred embodiment, the clutch member is secured against rotation with respect to the housing. The clutch member may be rotationally locked with respect to the housing. During mechanical cooperation of the dose member and the clutch member, rotational movement of the dose member with respect to the clutch member in the first direction is prevented. Rotational movement of the dose member with respect to the clutch member in the second direction opposite to the first direction is expediently allowed. A uni-directional friction clutch mechanism, which permits relative rotational movement between dose member and clutch member in one direction only, may be formed between clutch member and dose member during mechanical cooperation when the clutch member is in the clutch stop position. When the clutch member is out of the clutch stop position, the dose member may rotate with respect to the clutch member in the first direction and in the second direction.

The clutch member may follow displacement of the dose member in the proximal direction with respect to the housing during setting of the dose. The clutch member may follow displacement of the dose member in the distal direction with respect to the housing during delivery of the dose.

In another preferred embodiment, the stop member is displaced in the distal direction with respect to the housing when delivering the dose of the drug. Thereby, the clutch stop position is preferably displaced in the distal direction. The clutch stop position may, in particular, be displaced towards the clutch member. Thereby, the distance between clutch member and clutch stop position may be reduced. As the position of the stop member with respect to the distal end of the housing and/or of the cartridge may be indicative of the amount of drug currently available in the cartridge, setting of a dose that exceeds the available amount is prevented, because, before a dose exceeding the actually available amount could be set, the clutch member has already moved into the clutch stop position and mechanically cooperates with the dose member to prevent further proximal displacement of the dose member. Further proximal displacement of the dose member, however, would be necessary for increasing the size of the dose.

During dose setting, dose member and clutch member may be displaced in the proximal direction from a distal initial position to a proximal end position. The proximal end position may correspond to the size of the set dose. A maximum proximal end position may correspond to the maximum dose which may be set to be delivered by the device. Of course, the maximum dose is expediently smaller than the amount of drug initially provided for in the still unused drug delivery device.

During dose delivery, the stop member may be successively driven in the distal direction and, eventually, reach a position which is between the distal initial position and the maximum proximal end position of the clutch member. When a subsequent dose is set, the clutch member may be stopped in the stop position, for example by abutting the stop member during setting of the dose, thereby preventing setting of an excessive dose which could not be delivered.

The clutch member may be connected to the dose member. A connection member may be provided for connecting the clutch member to the dose member. The connection member may be provided with one or more guide features that may be configured and arranged to prevent rotational movement of the connection member with respect to the housing. The connection member may be rotationally locked to the clutch member. Thus, the clutch member cannot rotate with respect to the connection member.

In another preferred embodiment, the assembly comprises a piston rod. The piston rod may be configured to be displaced in the distal direction with respect to the housing for delivering the dose. The clutch stop position may be displaced in the distal direction with respect to the housing together with the piston rod. In particular, the stop member may be integrated in or connected to the piston rod. The stop member may be firmly connected to the piston rod. The piston rod may rotate and be displaced in the distal direction with respect to the housing. The piston rod may be threadedly connected to the housing or an insert thereof, for this purpose.

The stop member and/or the piston rod is preferably secured against displacement in the proximal direction during setting and/or delivery of the dose.

The stop member may be a protrusion of the piston rod. In particular, the stop member may be provided for by means of the distal end of a, preferably protruding, drive thread of the piston rod. The drive thread may determine the rotation angle, by which the piston rod is rotated with respect to the housing when it is driven by a drive member. The piston rod may comprise a displacement thread. The displacement thread is preferably different from the drive thread. For example, the drive thread may be a male thread and the displacement thread may be a female thread. Drive thread and displacement thread may have different leads. The displacement thread is expediently provided for determining the displacement of the piston rod with respect to the housing in the distal direction. The displacement thread may be arranged further away from a proximal end of the piston rod than the drive thread. The drive thread may be arranged further away from a distal end of the piston rod than the displacement thread.

In a further preferred embodiment, the assembly comprises a dose dial member. The dose dial member may be rotatable in the first direction and/or displaceable in the proximal direction with respect to the housing for setting of the dose. The dose member may follow rotational movement of the dose dial member and movement of the dose dial member in the proximal direction with respect to the housing during setting of the dose. The dose dial member may be splined to the dose member during setting of the dose.

Further features, expediencies and advantageous refinements become apparent from the following description of the exemplary embodiment in connection with the figures.

Like elements, elements of the same kind and identically acting elements may be provided with the same reference numerals in the figures.

Figure 1:
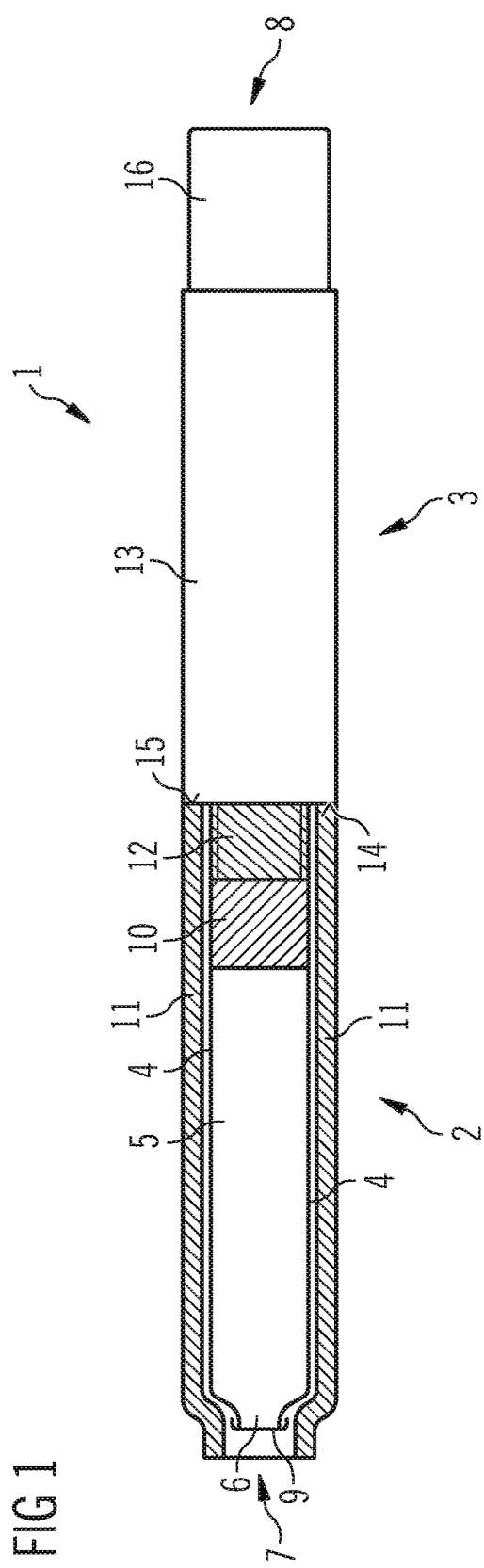
FIG. 1 shows an exemplary embodiment of a drug delivery device on the basis of a partly sectional view.

Turning now to FIG. 1, a drug delivery device 1 comprises a cartridge unit 2 and a drive unit 3. The cartridge unit 2 comprises a cartridge 4. A drug 5 is retained in the cartridge 4. The drug 5 is preferably a liquid drug. The cartridge 4 preferably comprises a plurality of doses of the drug 5. The drug 5 may comprise insulin, such as a short-acting or a long-acting insulin, heparin, or growth hormones, for example. The cartridge 4 has an outlet 6 at its distal end. Drug 5 may be dispensed from the cartridge through outlet 6. The device 1 may be a pen-type device, in particular a pen-type injector. The device 1 may be a disposable or a reusable device. The device 1 may be a device configured to dispense fixed doses of the drug or variable, preferably user-settable, doses. The device 1 may be a needle-based or a needle free device. The device 1 may be an injection device.

The term "distal end" of the drug delivery device 1 or a component thereof may refer to that end of the device or the component which is closest to the dispensing end of the device 1. The term "proximal end" of the drug delivery device 1 or a component thereof may refer to that end of the device or the component which is furthest away from the dispensing end of the device. In FIG. 1, the distal end of the device 1 was assigned reference numeral 7 and the proximal end of the device was assigned reference numeral 8.

The outlet 6 may be covered by a membrane 9, which may protect the drug 5 against external influences during storage of the cartridge. The membrane 9 is expediently impermeable for the drug. For drug delivery, membrane 9 may be penetrated, e.g. pierced. For example, membrane 9 may be pierced by a needle unit (not explicitly shown). The needle unit may be (releasably) attached, e.g. screwed, to the distal end of the cartridge unit 2. The needle unit may provide for fluid communication from the inside of the cartridge 4 to the outside of the cartridge through outlet 6.

A piston 10 is retained within the cartridge 4. The piston 10 is movable with respect to the cartridge. The piston 10 may seal the drug 5 within the cartridge. The piston 10 expediently seals the interior of the cartridge 4 proximally. Movement of the piston 10 with respect to the cartridge 4 in the distal direction causes drug 5 to be dispensed from the cartridge through outlet 6 during operation of the device.

The cartridge unit 2 furthermore comprises a cartridge retaining member 11. The cartridge 4 is retained within the cartridge retaining member 11. The cartridge retaining member 11 may stabilize the cartridge 4 mechanically. Additionally or alternatively, the cartridge retaining member 11 may be provided with a fixing member (not explicitly shown) for attaching the cartridge unit 2 to the drive unit 3.

The cartridge unit 2 and the drive unit 3 are secured to one another, preferably releasably secured. A cartridge unit 2 which is releasably secured to the drive unit may be detached from the drive unit 3, for example in order to allow for providing for a new cartridge 4, if all of the doses of drug which once were in the cartridge formerly attached to the drive unit 3 have already been dispensed. The cartridge retaining member 11 may be releasably secured to the drive unit 3 via a thread, for example.

Alternatively, the cartridge retaining member 11 may be dispensed with. It is particularly expedient, in this case, to apply a robust cartridge 4 and to attach the cartridge directly to the drive unit 3.

The drive unit 3 is configured for transferring force, preferably user-exerted force, particularly preferably manually exerted force, to the piston 10 for displacing the piston 10 with respect to the cartridge 4 in the distal direction. A dose of drug may be dispensed from the cartridge in this way. The size of the delivered dose may be determined by the distance by which the piston 10 is displaced with respect to the cartridge 4 in the distal direction during dose delivery.

The drive unit 3 comprises a drive mechanism. The drive mechanism comprises a piston rod 12. The piston rod 12 may be configured for transferring force to the piston 10, thereby displacing the piston in the distal direction with respect to the cartridge 4. A distal end face of the piston rod 12 may be arranged to abut a proximal end face of the piston 10. Alternatively, a bearing member (not explicitly shown) may be arranged to advance the piston 10, preferably to abut the proximal end face of the piston 10. The bearing member may be arranged between piston 10 and piston rod 12. The bearing member may be fixed to the piston rod 12 or may be a separate member. If the piston rod 12 is configured to be rotated during operation of the device, for example during dose delivery, it is particularly expedient to provide for a bearing member. The bearing member may be axially displaced together with the (rotating) piston rod 12 with respect to the cartridge 4. The piston rod 12 may be rotatable with respect to the bearing member. In this way, the risk that the rotating piston rod 12 drills into the piston 10 and thereby damages the piston is reduced. Accordingly, while the piston rod 12 rotates and is displaced with respect to the housing, the bearing member is preferably only displaced axially, i.e. does not rotate. The piston rod 12 may be bounded by the bearing member.

The drive unit 3 comprises a housing 13 which may be part of the drive mechanism and/or house parts of the drive mechanism. The piston rod 12 may be retained in the housing 13. A proximal end side 14 of the cartridge unit 2 may be secured to the drive unit 3 at a distal end side 15 of the housing 13, for example via a threaded connection. Housing 13, cartridge 4 and/or cartridge retaining member 11 may have a tubular shape.

The term "housing" shall preferably mean any exterior housing ("main housing", "body", "shell") or interior housing ("insert", "inner body") which may have a unidirectional axial coupling to prevent proximal movement of specific components. The housing may be designed to enable the safe, correct, and comfortable handling of the drug delivery device or any of its mechanism. Usually, it is designed to house, fix, protect, guide, and/or engage with any of the inner components of the drug delivery device (e.g., the drive mechanism, cartridge, piston, piston rod), preferably by limiting the exposure to contaminants, such as liquid, dust, dirt etc. In general, the housing may be unitary or a multipart component of tubular or non-tubular shape.

The term "piston rod" shall preferably mean a component adapted to operate through/within the housing, which may be designed to transfer axial movement through/within the drug delivery device, preferably from the drive member to the piston, for example for the purpose of discharging/dispensing an injectable product. Said piston rod may be flexible or not. It may be a simple rod, a lead-screw, a rack and pinion system, a worm gear system, or the like. "piston rod" shall further mean a component having a circular or non-circular cross-section. It may be made of any suitable material known to a person skilled in the art and may be of unitary or multipart construction.

The drive unit 3 comprises a dose part 16. The dose part 16 is movable with respect to the housing 13. The dose part 16 may be movable in the proximal direction with respect to the housing 13 for setting of a dose of the drug 5 which is to be delivered and, in particular, in the distal direction with respect to the housing for delivering the set dose. The dose part 16 is preferably connected to the housing 13. The dose part 16 may be moved (displaced) between a proximal end position and a distal end position with respect to the housing 13 (not explicitly shown). The distance by which the dose part 16 is displaced with respect to the housing 13 during setting of the dose may determine a size of the dose. The (maximum) proximal end position and the distal end position of the dose part 16 may be determined by a respective stop feature which may limit the proximal or distal travel of the dose part with respect to the housing 13. The device 1 may be a variable dose device, i.e. a device configured for delivering doses of the drug of different, preferably user-settable, sizes. Alternatively, the device may be a fixed dose device.

The device 1 may be a manually, in particular non-electrically, driven device. The (user-applied) force which causes the dose part 16 to be moved with respect to the housing 13 in the distal direction may be transferred to the piston rod 12 by the drive mechanism. For this purpose, other elements of the drive mechanism may be provided which are not explicitly shown in FIG. 1. The drive mechanism is preferably configured not to move the piston rod 12 with respect to the housing 13 when the dose part is moved in the proximal direction with respect to the housing for setting of the dose.

Several doses of the drug 5 may be dispensed from the cartridge 4. As the piston 10 successively advances towards the distal end of the cartridge 4, the amount of drug remaining in the cartridge 4, which is still available for dose delivery, is reduced. Accordingly, the situation may arise that a user sets a desired dose of the drug 5 which he intends to (self-) administer, but the amount of drug still left in the cartridge is not sufficient for delivering the desired dose. Thus, if a user is allowed to set a dose that exceeds the amount of drug left in the cartridge, the risk of administering a wrong dose of the drug, e.g. a dose which is less than the desired dose, is increased. Of course, administration of a wrong dose may have fatal, for example lethal, consequences for the user. Thus, it is desirable to provide for an end stop mechanism, for example a safety mechanism, which prevents setting of a dose of a drug which dose exceeds the actually available amount of drug 5 in the cartridge.

An embodiment of an end stop mechanism or end stop assembly, which is suitable for preventing setting of a dose of the drug 5 which exceeds the amount of drug available in the cartridge for dispense is described in conjunction with FIGS. 2 to 10 which also relate to a drug delivery device 1. The drug delivery device 1 illustrated therein may largely correspond to the device described in conjunction with FIG. 1, with the drive mechanism and, of course, the end stop mechanism being shown in more detail.

Figure 2:
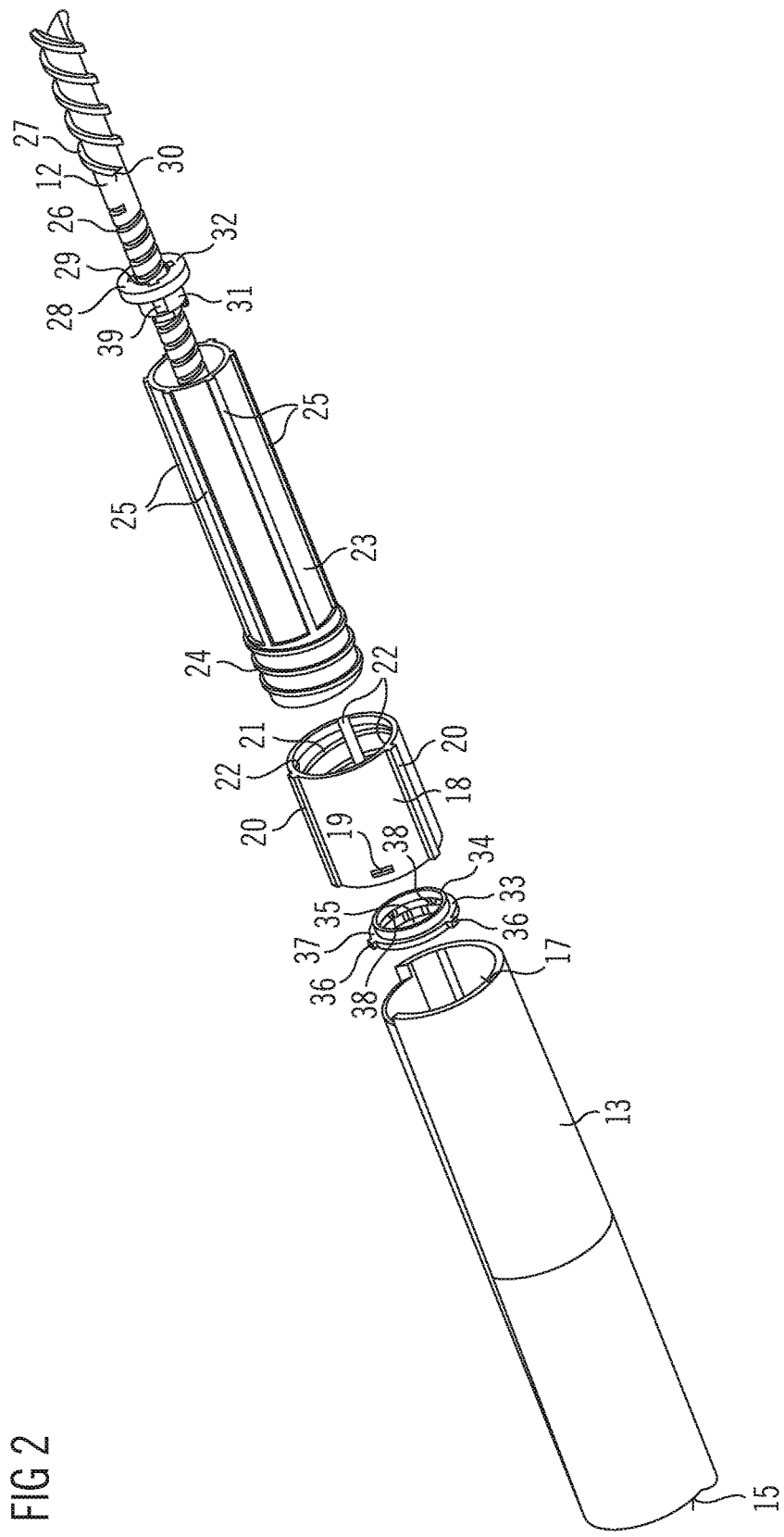
FIG. 2 shows an exploded view of parts of the drug delivery device.

In the exploded view of FIG. 2, housing 13 is shown with its distal end 15 and its proximal end 17. Housing 13 is preferably configured to retain further elements of the drug delivery device.

An insert member 18 is configured to be retained within housing 13. Insert member 18 may be secured against axial and rotational movement with respect to the housing 13. On an outer surface, insert member 18 may be provided with one or more fixing elements 19, for example snap-fit elements. Fixing elements 19 may be configured to engage corresponding inner fixing means in the housing (not explicitly shown). Fixing elements 19 may protrude radially from insert member 18. The insert member 18 is provided with one or more (outer) guide members 20, which may extend axially. Guide members 20 may be provided for allowing for inserting the insert member 18 in and/or securing it to the housing 13 (only) in a predetermined orientation. Guide members 20 may engage corresponding guide features in the housing 13 when insert member 18 is inserted in the housing 13 (not explicitly shown in FIG. 2). The insert member 18 may be an insert sleeve, for example. The insert member 18 may comprise a (inner) thread 21. Thread 21 may be a helical thread. One or more (inner) guide tracks 22 may be provided by the insert member 18, in particular on an inner surface thereof. Guide tracks 22 may interrupt thread 21. Guide tracks 22 may extend axially. Instead of providing for a separate insert member 18 as illustrated, thread 21 and/or guide tracks 22 may be provided for in the housing 13.

The drug delivery device 1 comprises a dose member 23. Dose member 23 is configured to be displaced in the proximal direction with respect to the housing 13 during setting of the dose of the drug 5 and/or in the distal direction with respect to the housing during delivery of the dose. Dose member 23 is provided with a (outer) thread 24. Thread 24 may be arranged in the distal end section of the dose member 23. Thread 24 may be arranged to engage thread 22 of the insert member 18. Dose member 23 may be a sleeve, for example. Dose member 23 may rotate in a first direction with respect to the housing during setting of the dose, thereby, in particular, being displaced in the proximal direction with respect to the housing on account of the threaded engagement to the insert member 18. During dose delivery, dose member 23 may rotate in a second direction opposite to the first direction with respect to the housing 13, thereby, in particular, being displaced in the distal direction with respect to the housing. Dose member 23 may be displaced in the proximal direction during dose setting from a distal initial position to a proximal end position and during dose delivery in the distal direction from the proximal end position back into the initial position.

The dose member 23 comprises one or more (outer) guide members 25, e.g. guide ribs. Guide members 25 may extend axially. Guide members 25 may be arranged in the proximal section of the dose member 23 as seen from thread 24. Guide members 25 may be configured to engage corresponding guide slots in a dose dial member (not explicitly shown in FIG. 2, see guide slots 50 in FIG. 7, for example). The dose member 23 and the dose dial member may be splined to one another when the device is assembled. Thus, relative rotational movement between dose member 23 and dose dial member is prevented. Relative axial movement between dose member 23 and dose dial member is allowed.

Additionally, the piston rod 12 is shown in FIG. 2. The piston rod 12 is provided with two different threads, displacement thread 26 and drive thread 27. Drive thread 27 may be arranged further away from the distal end of piston rod 12 than displacement thread 26. Drive thread 27 may be arranged in the proximal end section of the piston rod 12. Displacement thread 26 may be arranged in the distal end section of the piston rod 12. Displacement thread 26 may determine the axial displacement of the piston rod 12 when the piston rod 12 rotates and is axially displaced with respect to the housing. The drive thread may, for example due to interaction with a drive member (not explicitly shown in FIG. 2) determine the rotation angle by which the piston rod 12 is rotated. Displacement thread and drive thread may have a different hand and/or different leads. Drive thread 27 may be a double-thread. Drive thread 27 and/or displacement thread 26 may be a helical thread. Drive thread 27 preferably protrudes further in the radial direction from piston rod 12 than displacement thread 26.

Furthermore, the drug delivery device 1 comprises a clutch member 28. The clutch member 28 is configured to be connected to the dose member 23. The clutch member may be connected to the dose member 23 for following movement of the dose member in the proximal direction with respect to the housing during setting of the dose and/or in the distal direction with respect to the housing during delivery of the dose. The dose member 23 may rotate with respect to the clutch member 28 and, in particular, with respect to the housing 13. The clutch member 28 is secured against (any) rotational movement with respect to the housing 13. Axial movement of clutch member 28 with respect to the housing is allowed. Clutch member 28 may be a sleeve, for example. The clutch member has an opening 29. Opening 29 may be a central opening. Opening 29 is configured for the piston rod 12 to pass through opening 29 when piston rod 12 is displaced in the distal direction for delivering the dose. Piston rod 12 is preferably configured for being secured against movement in the proximal direction during setting of the dose and/or during delivery of the dose. Accordingly, the position of a particular point on the piston rod with respect to the distal end of the cartridge may be indicative for the amount of drug available in the cartridge for delivery.

The device further comprises a stop member 30. The clutch member 28 may be arranged to mechanically cooperate with, for example to abut, stop member 30. Stop member 30 may define a clutch stop position for proximal displacement of the clutch member 28 with respect to the housing and/or with respect to the piston rod 12. Stop member 30 may be connected to or integrated in the piston rod 12. The position of the stop member 30 with respect to the distal end of the cartridge 4 may be indicative of the amount of drug available in the cartridge for dispense. Stop member 30 may be configured to abut a proximal face of the clutch member 28. Stop member 30 may be formed by means of drive thread 26, in particular a distal end thereof.

Opening 29 is expediently configured to permit relative axial and/or rotational movement of the piston rod 12 with respect to the clutch member 28 until clutch member 28 and stop member 30 may cooperate mechanically. Opening 29 extends through the clutch member 28 from its proximal end to its distal end. Clutch member 28 comprises a main body portion 31, e.g. a tubular portion. Clutch member 28 comprises a flange portion 32. Flange portion 32 protrudes radially from the main body portion 31. Flange portion 32 may be arranged at the proximal end section of main body portion 31. A proximal face of flange portion 32 may be configured for abutting stop member 30, in particular a distal end face thereof.

The drug delivery device may comprise a connection member 33. The connection member 33 may be provided for connecting the clutch member to the dose member 23. The clutch member 28 may be firmly connected to the dose member 23 by means of connection member 33. The connection member 33 has a main body portion 34, e.g. a tubular portion. The main body portion 34 may be adapted to be received within dose member 33. Connection member 33 may have a (central) opening 35. Piston rod 12 may travel through opening 35. The connection member may further comprise one or more (outer) guide features 36. Guide features 36 may be configured for engaging guide tracks 22 of insert member 18. Relative rotational movement between connection member 33 and housing 13 may be prevented in this way. Guide features 36 may be guide pins, for example. Guide features may protrude radially from connection member 33. Guide features 36 may be disposed about the perimeter of connection member 33. Connection member 33 may have a flange portion 37. Guide features 36 may protrude from the flange portion 37.

A proximal surface of connection member 33 may be arranged to abut a distal surface of dose member 23. Connection member 33 may comprise one or more (inner) connection features 38, for example snap features. Connection features 38 may protrude radially inwardly within opening 35 of connection member 33. Connection features 38 are expediently configured to engage one or more fixing members 39 provided in clutch member 28. Fixing members 39 are expediently provided in the main body portion 31 of the clutch member 28. Fixing members 39 may be snap slots, for example. When connection member 33 is connected to clutch member 28, relative rotational movement between connection member and clutch member is prevented. However, a proximal and a distal end stop, for example formed by a distal end surface and a proximal end surface of the fixing members 39 may limit relative axial movement between connection member 33 and clutch member 28. Dose member 23 may rotate in both directions with respect to clutch member and connection member when dose member 23 is not mechanically cooperating with clutch member 28 as it was described below and is further described below.

Figure 3:
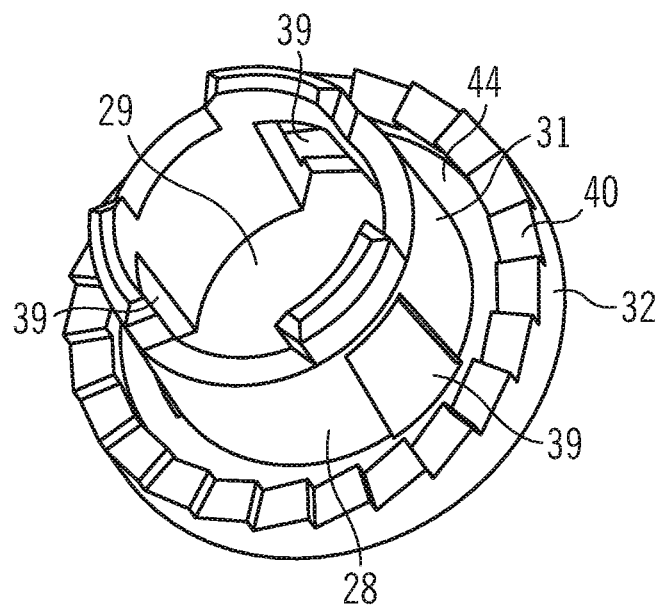
FIG. 3 shows an oblique view of an embodiment of a clutch member.
Figure 4:
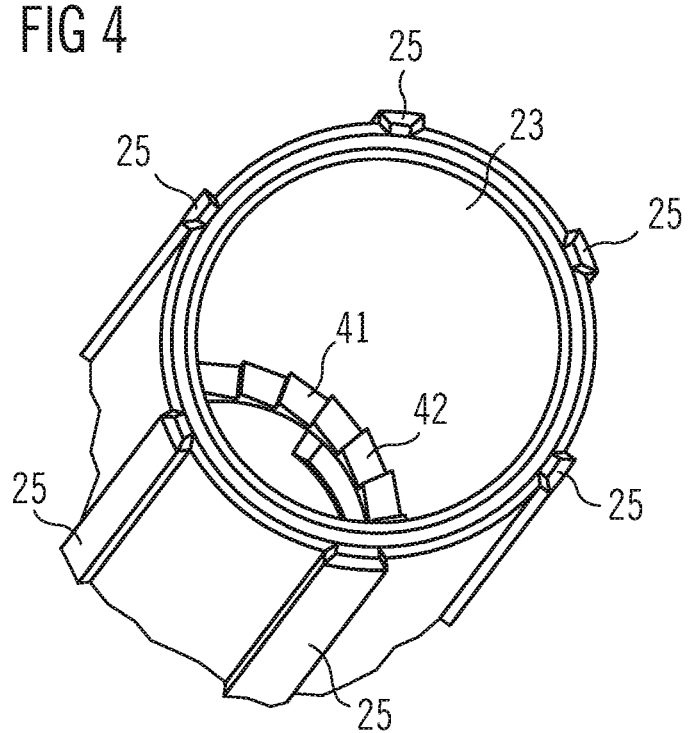
FIG. 4 shows an oblique view of an embodiment of a dose member.

FIG. 3 shows the clutch member 28 in more detail. Clutch member 28 has an engagement member 40. Engagement member 40 is configured to engage an engagement feature 41 of the dose member 23 (see the more detailed illustration of dose member 23 in FIG. 4). Engagement member 40 and/or engagement feature 41 may be a toothing comprising a plurality of teeth, preferably saw-teeth.

The respective toothing may be disposed about the perimeter of engagement feature 41 or engagement member 40, respectively. The teeth of the respective toothing may be oriented axially. The teeth of engagement member 40 are disposed along the perimeter of the clutch member 28, in particular along the flange portion 32 thereof. Engagement member 40 may be arranged on a distal surface of the clutch member 28, in particular on a distal surface of flange portion 32. The dose member 23 may comprise a flange portion 42. Flange portion 42 may protrude radially inwardly from the dose member 23. Flange portion 42 and/or engagement feature 41 may be arranged in the distal end section of dose member 23 and/or in the threaded section of the dose member, i.e. that section in which thread 24 is arranged. Flange portion 42 may be arranged in the distal (end) section of dose member 23. Teeth of the toothing of the engagement feature 41 may be configured to mate teeth of the toothing of engagement member 40. Thereby, dose member 23 and clutch member 28 may mechanically cooperate with one another.

When in mechanical cooperation (mechanical interaction), in particular, when engagement feature 41 and engagement member 40 are in engagement, relative rotational movement between dose member 23 and clutch member 28 is permitted only in one direction, preferably the second direction, i.e. the one in which the dose member rotates during dose delivery. Rotation of the dose member in the first direction which is necessary for setting of a dose is prevented on account of the engagement of dose member 23 and clutch member 28 and, in particular, on account of the clutch member 28 being secured against rotational movement with respect to the housing 13. For example, rotation of the dose member 23 in the first direction may be prevented by the steep sides of the respective teeth abutting. Rotational movement of the dose member 23 with respect to the clutch member 28 in the second direction may be allowed due to the beveled sides of the teeth sliding along each other. Accordingly, during mechanical cooperation, a uni-directional friction clutch mechanism may be formed between clutch member 28 and dose member 23 by mechanical cooperation of engagement feature 41 and engagement member 40.

Figure 5:
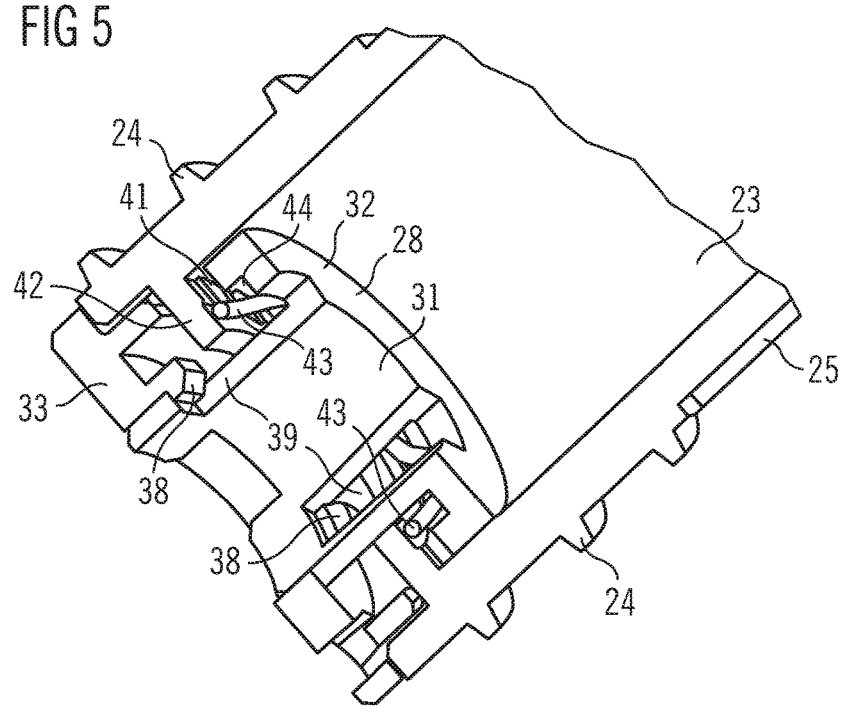
FIG. 5 shows an oblique sectional view of the clutch member connected to the dose member.

As shown in FIG. 5, the clutch member 28 is retained within and connected to dose member 23. Connection member 33 is (firmly) connected to clutch member 28, in particular by the connection features 38 engaging fixing members 39.

The main body portion 31 of the clutch member 28 may extend from the proximal side of the opening defined by flange portion 42 to the distal side thereof. The connection member 33 may be connected to the clutch member 28 via the main body portion 31 on the distal side of flange portion 32. The engagement member 40 and the engagement feature 41 face each other. Flange portion 42 and flange portion 32 overlap.

The engagement member 40 and the engagement feature 41 are biased away from one another to keep the dose member 23 and the clutch member 28 out of interaction. For this purpose, a clutch spring member 43 is provided for (cf. FIG. 5). Clutch spring member 43 may be a (helical) coil spring, for example. Clutch spring member 43 may be a pressure spring. Accordingly, during normal operation, i.e. when clutch member 28 is out of the clutch stop position, relative rotational movement in both directions is permitted, because the dose member 23 and the clutch member 28 do not mechanically cooperate with one another on account of the clutch spring member 43 preventing mechanical cooperation by keeping engagement member 40 at a predetermined distance from engagement feature 41. Clutch spring member 43 may bear on the clutch member 28, preferably on flange portion 32. Preferably, clutch spring member 43 is arranged within a notch 44, which may be provided for in clutch member 28 to receive an end of clutch spring member 32. Notch 44 may be provided in flange portion 32. Notch 44 may be formed between main body portion 31 and engagement member 40 (see FIG. 3, for example).

For connecting the clutch member 28 to the dose member 23, at first, the clutch spring member 43 is placed on clutch member 28, in particular in notch 44. Afterwards, clutch member 28 with clutch spring member 43 is introduced into dose member 23 until clutch spring member abuts flange portion 42 of dose member 23, in particular radially inwardly besides engagement feature 41. Afterwards, connection member 33 is firmly, and preferably permanently, joined to clutch member 28. Flange portion 42 of dose member 23 is arranged and, in particular, retained between clutch member 28 and connection member 33.

Figure 6:
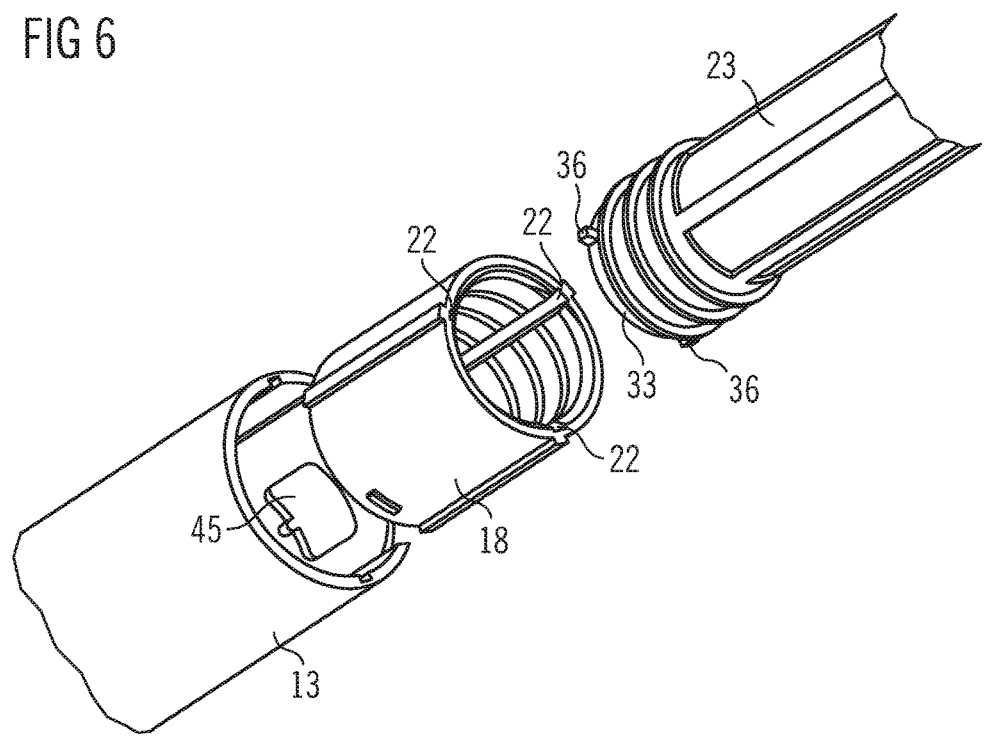
FIG. 6 shows an exploded view of parts of the drug delivery device.

FIG. 6 shows the dose member 23 and the connection member 33 as depicted in FIG. 5 with the (three) guide features 36 being oriented to engage the (three) guide tracks 22 of the insert member 18. A window 45 is provided in housing 13. Through window 45, information about a set dose, which may be provided for on a dose dial member (not explicitly shown in FIG. 6) may be made visible from outside of the housing.

Figure 7:
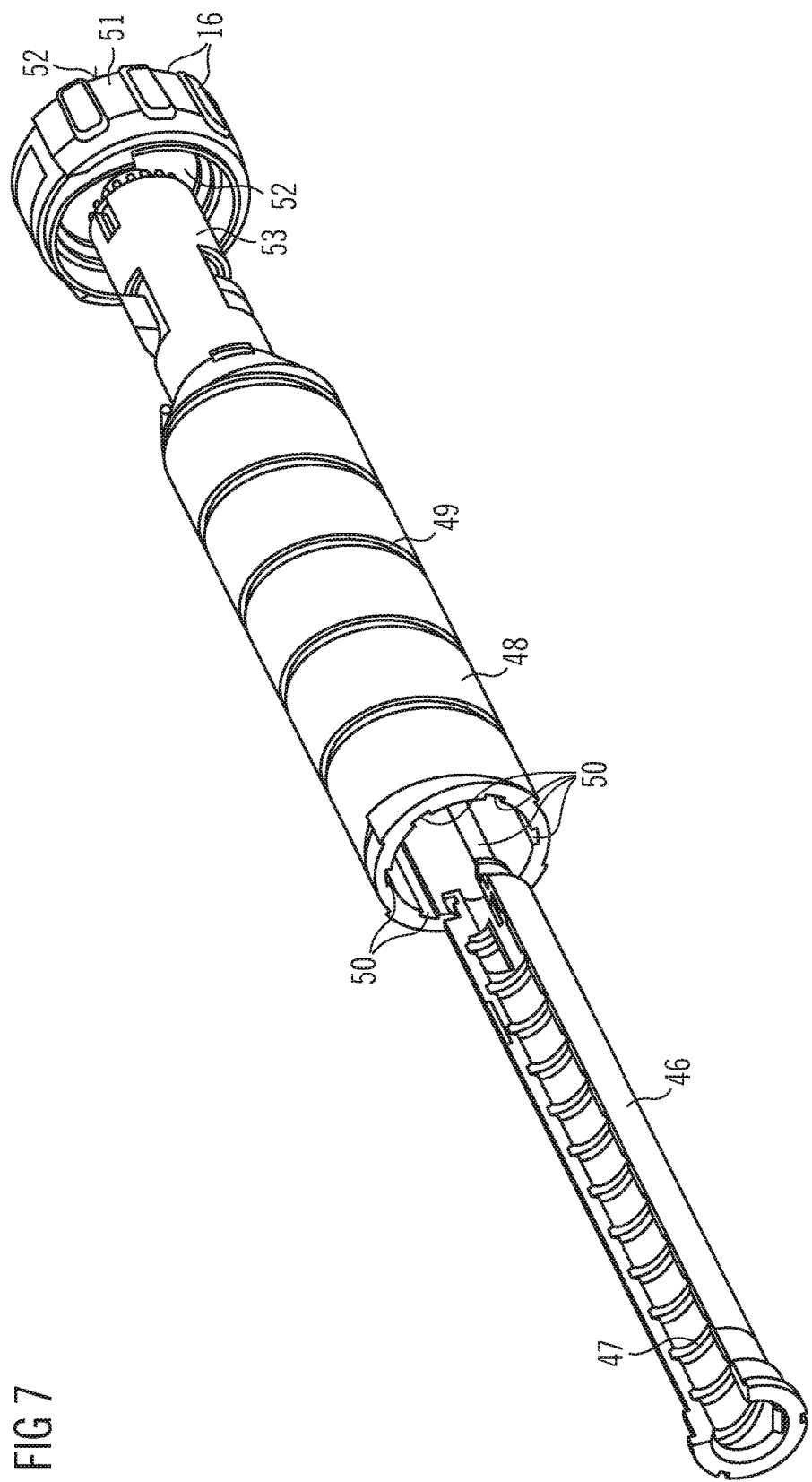
FIG. 7 shows an exploded view of parts of the drug delivery device.

FIG. 7 shows an exploded view of further parts of the drug delivery device 1. The drug delivery device 1 comprises a drive member 46. Drive member 46 may be a sleeve. Drive member 46 comprises a (internal) thread 47. Thread 47 may be a helical thread. Thread 47 may be adapted to cooperate with, in particular to abut, drive thread 27 of piston rod 12, preferably for putting piston rod 12 in rotation.

The drug delivery device comprises a dose dial member 48. Dose dial member 48 may be a sleeve. The dose dial member 48 has a (outer) thread 49. Thread 49 may be a helical thread. Thread 49 may determine the axial displacement of the dose dial member 48 in the proximal direction with respect to the housing 13 during setting of the dose and/or in the distal direction during delivery of the dose. Thread 49 preferably has a higher lead than thread 24. Accordingly, when rotated by the same angle in the same direction, dose member 23 is axially displaced by a distance which is smaller than the distance by which the dose dial member 48 is axially displaced. The outer surface of dose dial member 48 may be provided with indication elements, for example numerals. The numerals may indicate the size of the dose which is set by a user for delivery. In particular, the indication element rotated under window 45 may indicate the size of the dose which is dispensed when the currently set dose is delivered. The dose dial member 48 may comprise one or more (inner) guide slots 50. Dose member 23 may be splined to the dose dial member 48, for example by the respective guide member 25 engaging a corresponding guide slot 50. Guide slots 50 expediently extend axially.

The dose part 16 comprises a dose dial part 51. The dose part 16 comprises a dose button part 52. The dose dial part 51 may be rotated with respect to the housing 13 and, in particular, with respect to dose button part 52 for setting of a dose. Dose dial member 48 follows rotation of the dose dial part 51 during dose setting. The amount of rotation, e.g. the turns made, determines the size of the dose and/or the distance by which the dose dial member 48 is displaced in the proximal direction with respect to the housing 13.

The drug delivery device 1 comprises a coupling unit 53. Coupling unit 53 couples drive member 46 and dose dial member 48 such that drive member 46 follows rotation of the dose dial member 48 during setting of the dose. When the dose button part 52 is depressed for dose delivery, i.e. after the dose has been set, drive member 46 and dose dial member 48 are decoupled. The decoupling may be achieved by dose button part 52 interacting with coupling unit 53 when being depressed in the distal direction with respect to dose dial part 51. Accordingly, during dose delivery, dose dial member 48 rotates in the second direction and is displaced in the distal direction with respect to the housing. Drive member is displaced in the distal direction with respect to the housing without rotating. Thereby, thread 47 engages and/or abuts drive thread 27 of piston rod 12. Consequently, piston rod 12 rotates and is displaced in the distal direction with respect to the housing 13 on account of displacement thread 26. A similar drive mechanism is described in WO 2004/078239 A1, the disclosure content of which is incorporated herein by reference for all purposes. The (proximal section of the) dose member 23 may be arranged between drive member 46 and dose dial member 48.

Figure 8:
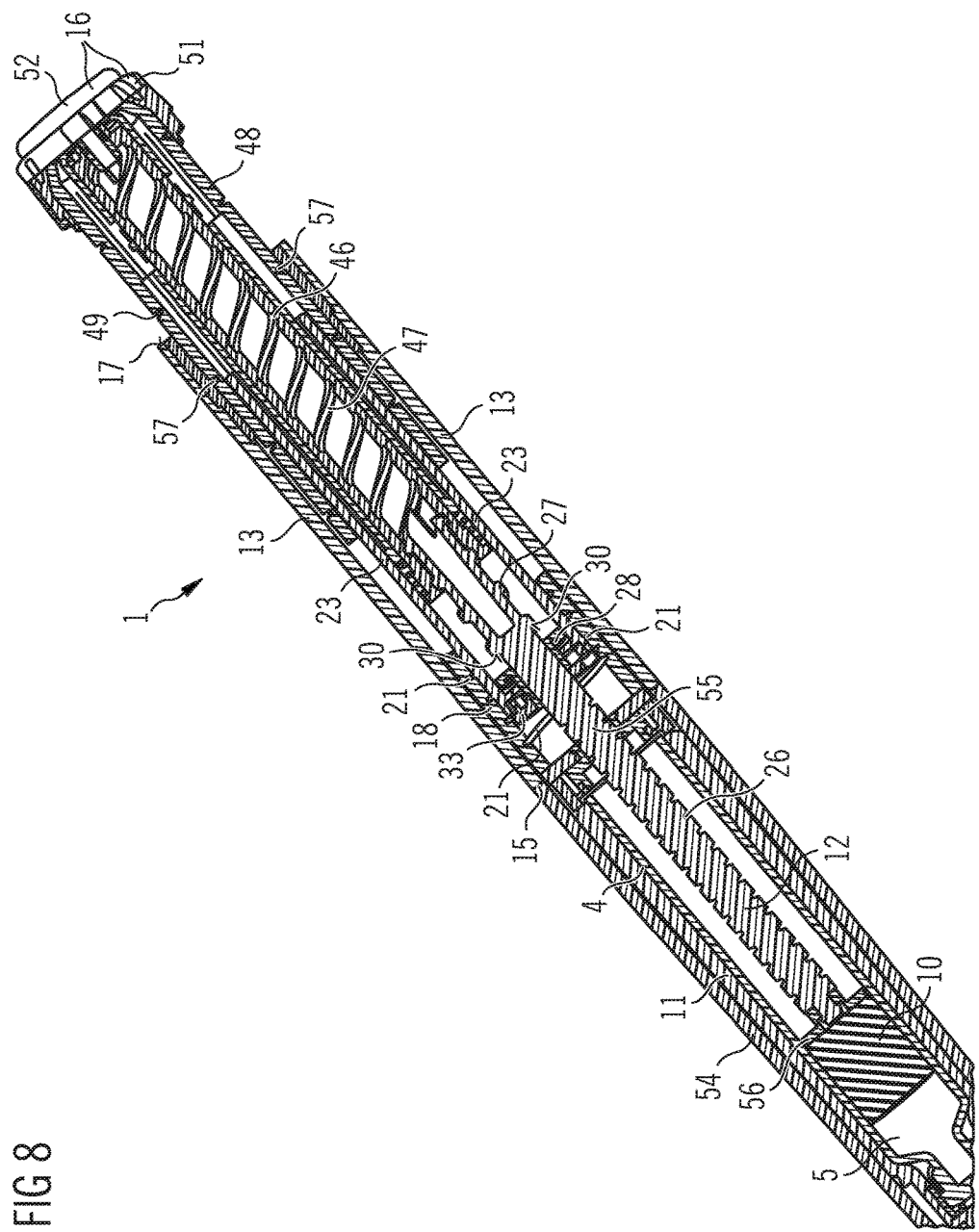
FIG. 8 shows an oblique sectional view of the assembled drug delivery device in a dose set position.
Figure 9:
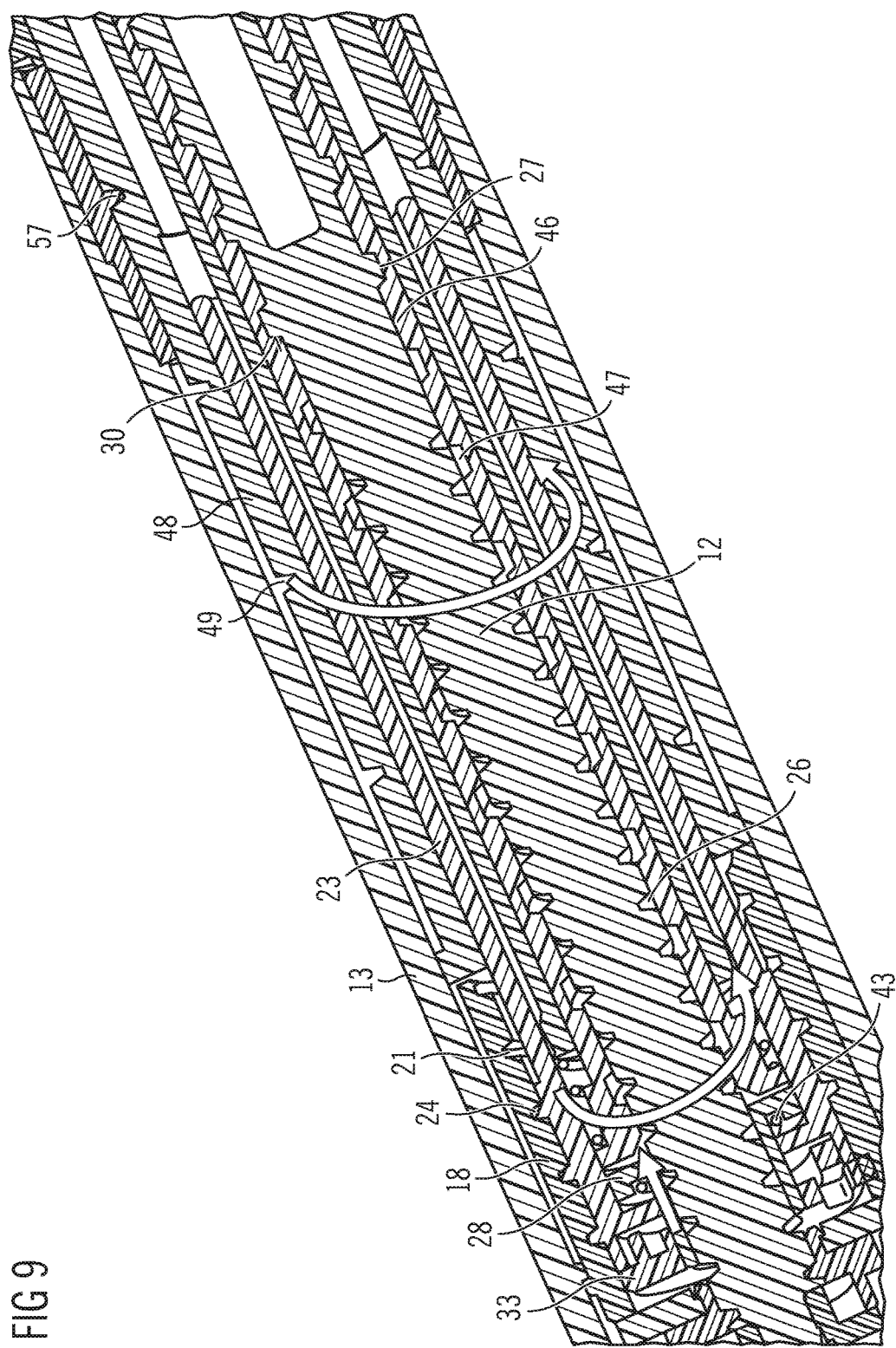
FIG. 9 shows a sectional view of a part of the assembled drug delivery device during dose setting.
Figure 10:
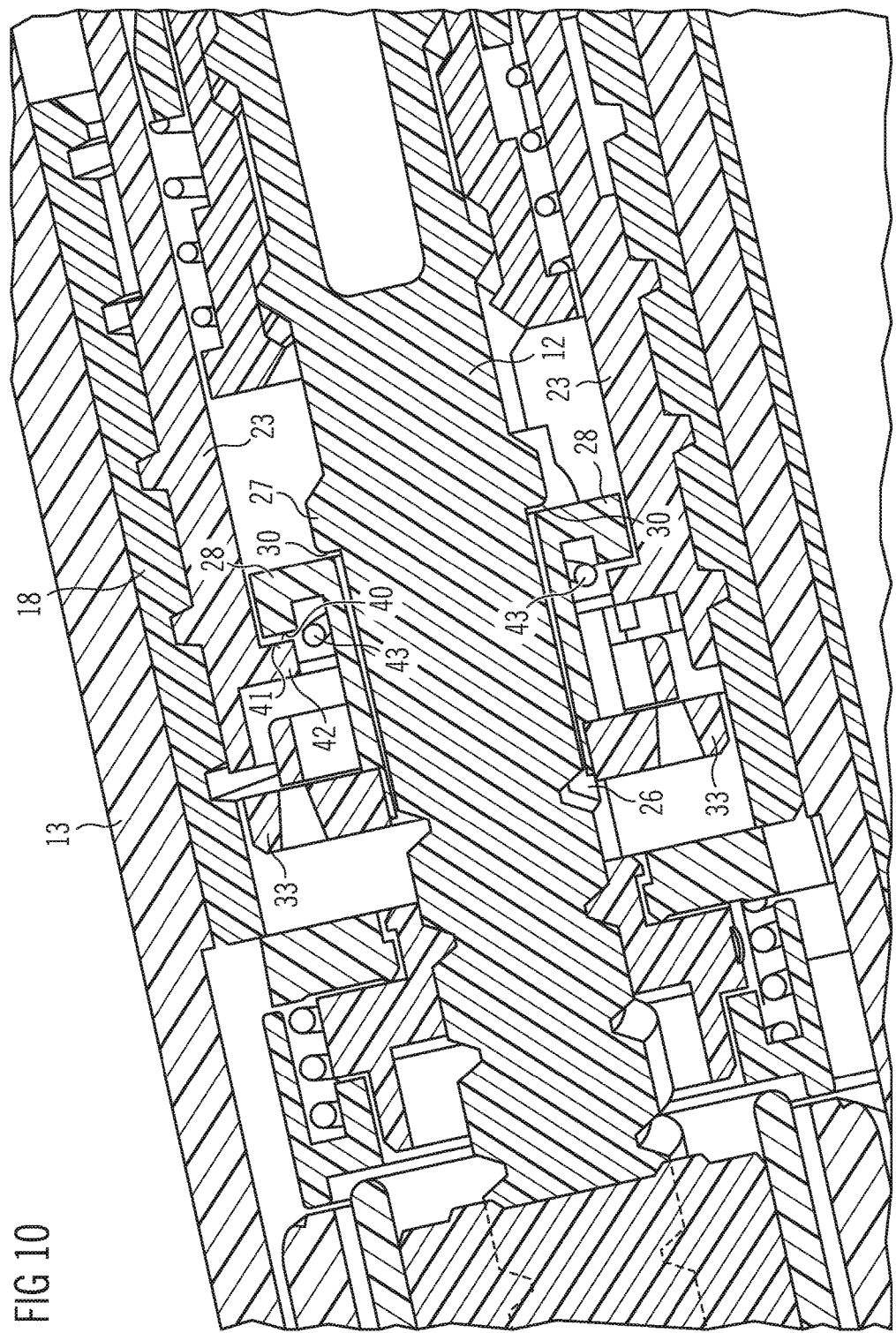
FIG. 10 shows a sectional view of a part of the assembled drug delivery device during dose setting.

FIG. 8 shows the drug delivery device 1 in assembled condition. As shown in FIG. 8, the cartridge 4 is covered by a cap 54, which may be removably attached to the device 1 and detached from the device for operation of the drug delivery device 1. The piston rod 12, in particular its displacement thread 26, is engaged with an opening 55, in particular a threaded and/or circular opening, which is provided in the housing 13. Accordingly, rotation of piston rod 12 results an axial displacement of the piston rod with respect to the housing 13. A bearing member 56 which may be connected to piston rod 12 is arranged between piston 10 and piston rod 12. The contact surface of piston rod 12 to piston 10 is increased by the bearing member. The piston rod 12 may be adapted to rotate with respect to bearing member 56. Thread 49 of dose dial member 48 engages an (inner) thread 57 of the housing 13 or an insert thereof.

In the situation shown in FIG. 8, a dose of drug 5 to be dispensed has been set by rotating dose dial member 48 in the first direction and displacing the dose dial member in the proximal direction with respect to the housing 13. When the dose dial member 48 is rotated, dose member 23, which is splined to dose dial member 48, follows this rotational movement. On account of the different threads 24 and 49, dose member 23 is displaced with respect to the housing 13 in the proximal direction by a distance which differs from the one the dose dial member is displaced. Preferably, dose member 23 is displaced in the proximal direction by a smaller distance than dose dial member 48. Clutch member 28 and connection member 33 follow displacement of the dose member 23 in the proximal direction. Clutch spring member 43 prevents clutch member 28 and dose member 23 from cooperating when stop member 30 is not abutting clutch member 28. Thus, during setting of the dose, dose dial member 48 and dose member 28 rotate in the first direction and are displaced in the proximal direction for setting a dose of the drug 5 (see FIG. 9 and the arrows therein which indicate these movements). During dose setting, dose member 23, clutch member 28 and connection member 33 are displaced in the proximal direction with respect to the housing 13 and, in particular, with respect to the piston rod 12. Piston rod 12 remains stationary during dose setting, i.e. at a fixed axial position. Piston rod 12 does not rotate during dose setting. The clutch member 28 is displaced from a distal initial position to a proximal end position during dose setting with respect to the housing 13. The proximal end position is determined by the size of the set dose. A maximum proximal end position may be determined by a maximum dose which may be set, e.g. by an end stop which limits rotation of the dose dial member 48 in the first direction with respect to the housing.

After the dose has been set, the dose button part 52 may be depressed and the dose may be dispensed. During delivery of the dose, piston rod 12 and, of course, the stop member 30 are displaced in the distal direction with respect to the housing 13. During dose delivery, clutch member 28, connection member 33 and dose member 23 are moved back into the distal initial position. Once the stop member 30 is arranged between the distal initial position of the clutch member 28 and the maximum proximal end position of the clutch member 28, the clutch member 28 may abut the stop member 30 during setting of the dose (see FIG. 10). If clutch member 28 and stop member 30 are in abutment, further rotation of the dose member 23 in the first direction moves engagement member 40 and engagement feature 41 in engagement against the force of clutch spring member 43. When in engagement, further rotation of the dose member 23 with respect to the clutch member 28 and thus also with respect to the housing 13 in the first direction is prevented on account of the clutch member 28 being secured against rotation with respect to the housing. Consequently, dose dial member 48 is prevented from rotation with respect to the housing 13. Thus, further rotation of the dose dial member 48 in the first direction (the dose setting direction) which is necessary for increasing the size of the dose is prevented. As the position of the stop member 30 with respect to the distal end of the cartridge 4 is indicative of the amount of drug 5 remaining in the cartridge, setting of a desired dose of drug which exceeds the actually available amount of drug is prevented. However, as rotation of the dose member 23 and, in particular, the dose dial member 48 in the second direction with respect to the housing 13 (the dose delivery direction) is still allowed, the set dose, i.e. the amount which was available in the cartridge, may be dispensed and is not wasted.

The scope of protection of the invention is not limited to the examples given hereinabove. The invention is embodied in each novel characteristic and each combination of characteristics, which particularly includes every combination of any features which are stated in the claims, even if this feature or this combination of features is not explicitly stated in the claims or in the examples.

REFERENCE NUMERALS 1 drug delivery device
2 cartridge unit
3 drive unit
4 cartridge
5 drug
6 outlet
7 distal end of the device
8 proximal end of the device
9 membrane
10 piston
11 cartridge retaining member
12 piston rod
13 housing
14 proximal end of cartridge unit
15 distal end of housing
16 dose part
17 proximal end of housing
18 insert member
19 fixing member
20 guide member
21 thread
22 guide track
23 dose member
24 thread
25 guide member
26 displacement thread
27 drive thread
28 clutch member
29 opening
30 stop member
31 main body portion
32 flange portion
33 connection member
34 main body portion
35 opening
36 guide feature
37 flange portion
38 connection feature
39 fixing member
40 engagement member 41 engagement feature
42 flange portion
43 clutch spring member
44 notch
45 window
46 drive member
47 thread
48 dose dial member
49 thread
50 guide slot
51 dose dial part
52 dose button part
53 coupling unit
54 cap
55 opening
56 bearing member
57 thread

The invention claimed is:

1. An assembly for a drug delivery device, comprising:
a housing having a proximal end and a distal end;
a dose member which is displaceable in the proximal direction with respect to the housing for setting of a dose of a drug;
a clutch member which is displaced in the proximal direction with respect to the housing and does not rotate with respect to the housing when setting the dose; and
a stop member configured to (i) abut the clutch member and (ii) define a clutch stop position for the proximal displacement of the clutch member with respect to the housing, with the clutch member,
when in the clutch stop position, being prevented from further displacement in the proximal direction with respect to the housing,
wherein
the clutch member and the dose member are configured to mechanically cooperate with one another when the clutch member is in the clutch stop position,
thereby preventing further displacement of the dose member in the proximal direction with respect to the housing during setting of the dose.

2. An assembly according to claim 1,
wherein the dose member is threadedly connected to the housing, and
wherein the dose member is rotated in a first direction with respect to the housing and displaced in the proximal direction with respect to the housing for setting of the dose.

3. An assembly according to claim 1,
wherein rotation of the dose member in the first direction with respect to the housing for setting of the dose is prevented or stopped when the dose member and the clutch member cooperate mechanically.

4. An assembly according to claim 1,
wherein, during mechanical cooperation of the dose member and the clutch member,
rotational movement of the dose member with respect to the clutch member in the first direction is prevented,
whereas rotational movement of the dose member with respect to the clutch member in a second direction opposite to the first direction is allowed.

5. An assembly according claim 1,
wherein the clutch member follows displacement of the dose member in the proximal direction with respect to the housing during setting of the dose.

6. An assembly according to claim 1,
wherein the clutch member is connected to the dose member.

7. An assembly according to claim 1,
further comprising a piston rod that is configured to be displaced in the distal direction with respect to the housing for delivering the dose.

8. An assembly according to claim 7,
wherein the stop member is integrated in or connected to the piston rod.

9. A drug delivery device, comprising an assembly according to claim 1 and a cartridge containing the drug.

10. A drug delivery device according to claim 9,
wherein the cartridge has a proximal end and a distal end,
a piston is retained within the cartridge,
the piston being displaceable in the distal direction with respect to the cartridge for dispensing a dose of the drug from the cartridge.

11. An assembly according to claim 7,
wherein the piston rod comprises a bearing member.

12. An assembly according to claim 11,
wherein the piston rod comprises a unitary piston rod.

13. An assembly according to claim 7,
wherein the piston rod comprises a circular cross section.

14. An assembly according to claim 1, further comprising:
an insert member configured to be retained within the housing.

15. An assembly according to claim 14,
wherein the insert member is secured against axial movement with respect to the housing.

16. An assembly according to claim 14,
wherein the insert member is secured against rotational movement with respect to the housing.

17. An assembly according to claim 14,
wherein the insert member comprises one or more fixing elements.

18. An assembly according to claim 17,
wherein the one or more fixing elements comprise a snap-fit element.

19. An assembly according to claim 17,
wherein the one or more fixing elements engage corresponding inner fixing elements in the housing.

20. An assembly according to claim 17,
wherein the one or more fixing elements protrude axially from the insert member.

21. An assembly according to claim 14,
wherein the insert member is provided with one or more guide members.

22. An assembly according to claim 21,
wherein the one or more guide members comprises an outer guide member.

23. An assembly according to claim 21,
wherein the one or more guide members extend axially.

24. An assembly according to claim 21,
wherein the one or more guide members are provided for allowing for inserting the insert member in the housing in a predetermined orientation.

25. An assembly according to claim 21,
wherein the one or more guide members engage guide features in the housing when the insert member is inserted in the housing.

26. An assembly according to claim 14,
wherein the insert member comprises an insert sleeve.

27. An assembly according to claim 14,
wherein the insert member comprises a guide track.

28. An assembly according to claim 27,
wherein the guide track comprises an inner guide track.

29. An assembly according to claim 27,
wherein the guide track is provided along an inner surface of the insert member.

30. An assembly according to claim 1, wherein the dose member is provided with a thread at a distal end section of the dose member.

* * * * *